United States Patent
Gachelin et al.

(10) Patent No.: US 12,186,685 B2
(45) Date of Patent: Jan. 7, 2025

(54) SYSTEM AND METHOD FOR CHANGING A CONCENTRATION OF PARTICLES IN A FLUID

(71) Applicant: AENITIS TECHNOLOGIES, Mitry-Mory (FR)

(72) Inventors: Jérémie Gachelin, Arcueil (FR); Nicolas Bertin, Ermont (FR); Emmanuel Vincent, Mitry-Mory (FR)

(73) Assignee: AENITIS TECHNOLOGIES, Mitry-Mory (FR)

( * ) Notice: Subject to any disclaimer, the term of this patent is extended or adjusted under 35 U.S.C. 154(b) by 861 days.

(21) Appl. No.: 17/296,670

(22) PCT Filed: Dec. 11, 2019

(86) PCT No.: PCT/EP2019/084715
§ 371 (c)(1),
(2) Date: May 25, 2021

(87) PCT Pub. No.: WO2020/120605
PCT Pub. Date: Jun. 18, 2020

(65) Prior Publication Data
US 2022/0023776 A1    Jan. 27, 2022

(30) Foreign Application Priority Data
Dec. 11, 2018 (EP) .................................. 18306660

(51) Int. Cl.
*B01D 21/28* (2006.01)
*B01D 21/34* (2006.01)

(52) U.S. Cl.
CPC ........... *B01D 21/283* (2013.01); *B01D 21/34* (2013.01)

(58) Field of Classification Search
CPC .......... B01D 21/28; B01D 21/34; A61M 1/02; A61M 1/36; C02F 1/32
See application file for complete search history.

(56) References Cited

U.S. PATENT DOCUMENTS

2015/0110763 A1    4/2015  Leach
2015/0111277 A1*   4/2015  Hamman ............ A61M 1/3693
                                                422/534

FOREIGN PATENT DOCUMENTS

EP      2 492 011 A1     8/2012
WO   2017/191289 A1    11/2017

OTHER PUBLICATIONS

International Search Report and Written Opinion of the International Searching Authority issued on Mar. 11, 2020 in corresponding International application No. PCT/EP2019/084715; 8 pages.

* cited by examiner

*Primary Examiner* — Walter D. Griffin
*Assistant Examiner* — Cameron J Allen
(74) *Attorney, Agent, or Firm* — Maier & Maier, PLLC

(57) ABSTRACT

A system for changing a concentration of at least one group of particles in a fluid, which includes a first container and a second container; a first transfer device and a second transfer device, and an element for keeping the volume of fluid in the first and second containers constant. The first container is fluidly connected to an inlet of the first transfer device, and the second container is fluidly connected to an inlet of the second transfer device. The first and second transfer devices include a chamber associated with at least one acoustic wave generator for generating acoustic waves within the chamber; at least two outlets including a first outlet for fluid enriched with the particles and a second outlet for fluid depleted of the (Continued)

particles; the first outlet being fluidly connected to the first container and the second outlet being fluidly connected to the second container.

16 Claims, 3 Drawing Sheets

SYSTEM AND METHOD FOR CHANGING A CONCENTRATION OF PARTICLES IN A FLUID

FIELD

The present invention relates to the field of fluid fractionation and enrichment by changing the concentration of particles in said fluid. In particular, the present invention involves changing the concentration of a given group of particles in a fluid using a system associated with an acoustic wave generator.

BACKGROUND

Systems based on filtration or centrifugation processes are well known in the art for separation of components in particle suspensions, notably cell suspensions such as whole blood, bone marrow or cerebrospinal fluids, or mineral suspensions such as mine slurry or mud.

In a typical blood fractionation process, whole blood is collected in a first tube and is then centrifuged to separate whole blood into its components. By connecting empty tubes to the first tube and manipulating a valve, the blood components are transferred to the other tubes. Said blood components may be red blood cells, platelets, plasma and the like.

However, filtration or centrifugation of whole blood raises several issues. The high rotation speed of centrifugation allows stratification of the whole blood thereby separating its components but also induces strong shear on the cells. Blood cells may also be damaged by filtration as they are forced through membrane pores. Filtration and centrifugation processes are also expensive, require extensive cleaning of the equipment, are not 100% efficient to separate whole blood components, are time consuming and require burdensome manipulations of the samples.

Acoustophoretic separation of whole blood components overcomes many of these drawbacks. Indeed, it prevents damaging of blood components as it does not require any rotation or mechanical forces and acoustical forces applied are lower.

In a typical acoustophoretic separation of whole blood components, whole blood is introduced in a channel and an ultrasonic field is generated within said channel. This enables the creation of acoustic pressure nodes in the channel. The whole blood components migrate to the sound pressure nodes, allowing selective separation.

Document WO 2017/191289 discloses such an acoustophoretic separation of whole blood components using a multiple blood bag system. Said system comprises several blood collecting bags and transfer means for transferring fluid arranged in series. Whole blood is introduced in the system and is subjected to successive acoustophoretic separation in the transfer means, inducing separation of its components. However, such a system does not allow a 100% effective separation of whole blood components as it is not possible to perform cycles of separation and a part of the components can escape the acoustophoretic separation.

Similar problems occur in fields other than blood fractionation, such as water depollution or other fields in which a concentration of particles in a fluid has to be changed.

Having regard to the state of the art identified above, one object underlying the present invention is to provide a simple, non-expensive system allowing a change in a concentration of one or several groups of particles in a fluid, in particular a fractionation of a fluid, an enrichment of a fluid with one or several components, a depletion of a fluid of one or several components, with optimum efficiency.

Another object of the present invention is to provide a simple and fast method for changing a concentration of one or several groups of particles in a fluid.

SUMMARY

To this end, the present invention relates to a system for changing a concentration of at least one given group of particles comprised in a fluid, the system comprising:
  a first container and a second container;
  a first transfer device and a second transfer device, wherein the first container is fluidly connected to an inlet of the first transfer device and the second container is fluidly connected to an inlet of the second transfer device, each of the first and second transfer devices comprising:
    a chamber configured to be associated with at least one acoustic wave generator for generating acoustic waves within the chamber;
    at least two outlets comprising a first outlet for fluid enriched with said given group of particles and a second outlet for fluid depleted of said given group of particles;
  the first outlet being fluidly connected to the first container and the second outlet being fluidly connected to the second container; and
  means for keeping the volume of fluid in each of the first and second containers constant.

In the present invention, the expression "changing a concentration of at least one given group of particles comprised in a fluid" encompasses increasing said concentration or decreasing said concentration, in particular with the aim of fractionating, enriching the fluid with at least one given group of particles, or depleting the fluid of at least one given group of particles.

The system of the invention can be used to fractionate a fluid into a plurality of given groups of particles.

The particles of said given group of particles are selectively guided to the first outlet of each transfer device according to the wavelength of the acoustic waves generated and the geometry of the channel. For example, in the case of a chamber with three outlets, comprising a first central outlet and two second peripheral outlets, the particles are guided to the first central outlet.

In one embodiment, the system of the invention comprises flow control means for applying a controlled flow within the system, notably from the outlets of the containers to the inlets of the transfer devices and from the outlets of the transfer devices to the inlets of the containers.

According to one embodiment, said flow control means comprise a control unit, measurement means for performing measurements representative of the volume of fluid in the first container and/or the second container, and flowing means for imposing a flow of fluid within the system.

According to one embodiment, the control unit is configured to keep the volume of fluid in each of the first and second containers constant by regulating the flow rate of the fluid circulating in the system as a function of measurements representative of the volume of fluid in the first container and/or the second container. In this embodiment, the flow of the fluid in the system is preferably controlled at all times.

In one embodiment, the measurement means are configured to measure the volume of fluid in the first container and/or the second container, and/or the weight of the first container and/or the second container, and/or the fluid flow rate in the first container and/or the second container. For example, measurement means may be weighing scales, flow-meters or any other means for measuring a weight, a volume, a flow rate, or any other value representative of a volume known in the art.

In one embodiment, the measurements representative of the volume of fluid in the first container and/or the second container are measurements of the volume of fluid in the first container and/or the second container, and/or measurements of the weight of the first container and/or the second container, and/or measurements of the fluid flow rate in the first container and/or the second container. In particular, the fluid flow rate is advantageously measured at the inlet of the first container and/or at the inlet of the second container.

In one embodiment, the first container and/or the second container are weighed in real time to ensure that their weights stay constant and the flow rates are electronically regulated.

In one embodiment, the flowing means are configured to regulate flow rates at the inlets of the first and second containers and the first and second transfer devices. In this embodiment, said flowing means work in cooperation with the measurement means to ensure that the volume of fluid in each of the first and second containers is constant. Typically, the flow rate imposed by the flowing means is controlled by the measurement means that measure the volume of fluid in the containers, and/or the weights of the containers, and/or the fluid flow rate in the containers.

In one embodiment, the flowing means are located at the outlets of the first and second containers and the first and second transfer devices.

In one embodiment, the flowing means comprise a pump, such as for example a peristaltic pump, gear pump, centrifugal pump, diaphragm pump, rotary vane pump, piston pumps, pressure pumps, gravitational forces, and their derivatives. In one embodiment, the flowing means comprise valves. In this embodiment, said flowing means regulate the flow rates at the inlets of the first and second containers and of the chamber to prevent a complete emptying of the first and/or second containers.

In one embodiment, the fluid flow rate at the inlet of each of the first and second transfer devices is between 0.1 mL/min and 50 mL/min.

In one embodiment, the fluid flow rate at the inlet of each of the first and second containers is between 0.1 mL/min and 50 mL/min.

In one embodiment, the system of the invention comprises at least three outlets comprising a first central outlet for fluid enriched with said given group of particles and two second peripheral outlets for fluid depleted of said given group of particles. In this embodiment, upon application of an acoustic field in the chamber, the given group of particles migrates to the sound pressure node created in the center of the chamber and are delivered at the first central outlet, whereas other components of the fluid are delivered on the sides of the chamber at the second peripheral outlets.

In one embodiment, the system of the invention is a closed-loop system. In this embodiment, the fluid circulates several times in the system until the concentration of the given group of particles reaches a predefined level in the second container.

In one embodiment, said predefined level is equal to or lower than the purity requirements for said particles. Said requirements may be regulatory requirements or client requirements.

In one embodiment, the system of the invention is a closed-loop separator. It can be used to separate a given group of particles from a fluid and/or enrich said fluid with said group of particles.

In one embodiment, the system of the invention is sterile.

In one embodiment, the system of the invention is a closed system.

In one embodiment, the system is disposable. In this embodiment, the disposability ensures a good hygiene, regulatory compliance and saves time. In this embodiment, the system is changed after every use.

According to one embodiment, the system and all its parts are disinfectable. In this embodiment, the system can be disinfected using a cleaning bath, a disinfectant wipe, or any other means known by one skilled in the art.

In one embodiment, the system is a portable system. In this embodiment, the dimensions of the system and the connections between each part of said system allows an easy transportation of said system.

In one embodiment, the fluid is a liquid.

In one embodiment, the fluid is a biological fluid selected in the group comprising human and/or non-human cell suspension, cell cluster suspension, blood, whole blood, surgical blood, platelet rich plasma, buffy coat, urine, serum, lymph, fluidified feces, adipose tissue, bone marrow, cerebrospinal fluid, sperm, cord blood, milk, saliva, tissue, egg albumen, seashell mix, or a mixture thereof.

In one embodiment, the fluid can be, but is not limited to: a buffer medium, water, oil, mud, air, or a mixture thereof.

In one embodiment, the fluid comprised in the first container and/or second container is a biological fluid selected in the group comprising human and/or non-human cell suspension, blood, whole blood, surgical blood, platelet rich plasma, buffy coat, urine, serum, lymph, fluidified feces, adipose tissue, bone marrow, cerebrospinal fluid, sperm, cord blood, milk, saliva, tissue, egg albumen, seashell mix or a mixture thereof.

In one embodiment, the fluid comprised in the first container and/or second container can be, but is not limited to: a buffer medium, water, oil, mud, air, or a mixture thereof.

According to one embodiment, the buffer medium is an additive solution for preservation and/or for anticoagulation. According to one exemplary embodiment, the additive solution for preservation is for example SAG-Mannitol (SAGM), PAS III M or SSP+.

According to one exemplary embodiment, the additive solution for anticoagulation is for example a citrate-phosphate-dextrose solution (CPD).

In one embodiment, the particles are selected in the group comprising biological cells, dispersed cells in a dispersion medium, monodisperse or polydisperse cells, blood cells, platelets, red blood cells, white blood cells, cancer cells, stem cell, progenitor cells, bacteria, proteins, liposomes, organelles, cell clusters, viruses, vesicles, microparticles, nanoparticles, microbubbles, microbeads, microorganisms, parasites, algae, sand, sediment, dust, antibodies, powders, gametes, parasite eggs, plankton, tissue, fat, pollen, spores, metal particles, or a mixture thereof.

In the case of polydisperse cells, the size differences between cells may enable the cells to be separated according to the differences in their migration velocity toward the acoustic pressure node generated along the thickness of the chamber.

According to one embodiment, the biological fluid is whole blood and the system of the invention allows fractionating and enrichment with blood products such as red blood cells (RBC), white blood cells (WBC), platelets, blood plasma, such as platelet poor plasma (PPP) or platelet rich plasma (PRP), without centrifugation.

In one embodiment, the particles have an average size ranging from 1 nm to 1 mm Small proteins have typically an average size around 1 nm, whereas cell clusters can have an average size up to 1 mm.

In one embodiment, the wavelength of the acoustic waves is greater than the average size of the particles to be separated, preferably greater than or equal to ten times this average size.

In one embodiment, the thickness of the chamber is, at least at a position along the longitudinal axis at which the acoustic waves are generated, greater than or equal to ten times the average size of the particles to be separated.

In one embodiment, the fluid comprises more than one group of particles to be separated from the fluid, such as for example 2, 3, 4, 5, 6, 7, 8, 9, 10 groups of particles. In this embodiment, acoustic waves with distinct wavelengths are used to separate each group of particles from the fluid.

In one embodiment, the fluid is enriched with more than one group of particles, such as for example 2, 3, 4, 5, 6, 7, 8, 9, 10 groups of particles.

In one embodiment, the fluid is depleted of more than one group of particles, such as for example 2, 3, 4, 5, 6, 7, 8, 9, 10 groups of particles.

In one embodiment, the fluid in the first container can be enriched with at least one group of particles while the second container is enriched with at least another group of particles.

In one embodiment, the connections between the parts of the system are sterile.

In one embodiment, the first and second containers are each configured to comprise a fluid, the fluid comprised in the first container being enriched with at least one given group of particles and the fluid comprised in the second container being depleted of said group of particles.

In one embodiment, each of the first and second containers is a chamber, a bioreactor, a bottle, a bag, a pouch, a vial, a reservoir, a module, or a bottle into which a fluid is transferred, stored or collected.

In one embodiment, the first container and the second container have the same volume. In one embodiment, the first container and the second container have distinct volumes. In one embodiment, the ratio between the volume of the first container and the volume of the second container ranges from 0.1 to 10.

Controlling the volumes of fluid in the first and second container, or the ratio between said volumes allows the control of the final fluid collected in the first container in terms of volume of fluid and concentration of a given group of particles.

In one embodiment, the first container has at least one inlet and at least one outlet.

In one embodiment, the first container has one inlet configured to insert a fluid in said container, and to be fluidly connected to the first outlet of the chamber.

In one embodiment, the second container has at least one inlet and at least one outlet.

In one embodiment, the second container has one inlet configured to insert a fluid in said container, and to be fluidly connected to the second outlet of the chamber.

In one embodiment, the first container has two inlets: a first inlet configured to insert a fluid in said container, and a second inlet fluidly connected to the first outlet of the chamber.

In one embodiment, the second container has two inlets: a first inlet configured to insert a fluid in said container, and a second inlet fluidly connected to the second outlet of the chamber.

In one embodiment, the first and second containers are disposable. In this embodiment, the disposability ensures a good hygiene, regulatory requirements and saves time. In this embodiment, the first and second containers are changed after every use.

In one embodiment, the first and/or second container have a second inlet closed by a septum allowing to inject or sample its content using a needle.

In one embodiment, the first and/or second container have a second inlet allowing them to be fluidly connected to another container in order to distribute its content into the first and/or second container prior to the separation process.

In one embodiment, the first and/or second container is fluidly connected to at least one vein puncture needle. In this embodiment, said vein puncture needle can be connected to the vein of a subject. The vein puncture needle may be used to transfer the blood from said subject to the first and/or second container, and to transfer the enriched blood back to said subject after at least one passage in the transfer device.

In one embodiment, the first and second containers and/or the chamber comprise a biocompatible, antimicrobial and/or hypoallergenic material. A biocompatible material is advantageous as it allows contact with a biological fluid. An antimicrobial and/or hypoallergenic material is advantageous as it prevents growth of undesirable microorganisms and/or allergy upon contact with the fluid.

In one embodiment, examples of said material comprise but are not limited to: polymer, such as for example an organic polymer or an inorganic polymer; metal, such as for example stainless steel; gel, such as for example hydrogel; glass, such as for example fused quartz, pyrex; crystal, such as for example silicon; ceramic, such as for example silicon carbide; or a mixture thereof.

In one embodiment, examples of polymer comprise but are not limited to: polyurethane, silicone, polyethylene, poly(methyl methacrylate) (PMMA), polymethylpentene, polystyrene, polycarbonate, polydimethylsiloxane, or a mixture thereof.

In one embodiment, the first and second transfer devices are not arranged in series. In this embodiment, the fluid comprised in the containers is not treated successively with the acoustic waves in the first and second transfer devices.

In one embodiment, the first and second transfer devices are arranged in parallel. In this embodiment, the fluid comprised in the containers is treated simultaneously with the acoustic waves in the first and second transfer devices before being collected in the first or second container, ensuring that the volume of fluid in each of said containers stays constant at all times.

In one embodiment, the first and second transfer devices are disposable. In this embodiment, the disposability ensures a good hygiene, regulatory requirements and saves time. In this embodiment, the first and second containers are changed after every use.

In one embodiment, each of the first or second transfer devices comprises at least one inlet in fluid communication with the chamber, said inlet being fluidly connected to one of the first or second containers.

In one embodiment, the chamber of each transfer device extends along a longitudinal axis, has a cross section with a width measured along a first transverse axis and a thickness measured along a second transverse axis perpendicular to the first transverse axis, the width being greater than or equal to the thickness, the chamber having first and second walls along the second transverse axis.

In one embodiment, the chamber has a cylindrical shape, or a parallelepipedal shape.

In one embodiment, the chamber is a channel.

In one embodiment, the width/thickness ratio of the chamber is greater than 1.

The thickness of the chamber is equal to the distance, measured along the second transverse axis, separating the first and second walls.

In one embodiment, the thickness of the chamber is ranging from 10 μm to 1 mm.

In one embodiment, the chamber is a microchannel, i.e. the chamber has a thickness equal to or inferior than 1 mm over the whole of its length.

In one embodiment, the acoustic waves have a wavelength $\lambda$ and the thickness of the chamber is substantially equal to a multiple of $\lambda/4$.

In one embodiment, the thickness of the chamber is constant or variable along the longitudinal axis of the chamber.

In one embodiment, the width of the chamber is greater than 0.1 mm.

In one embodiment, the width of the chamber is constant or variable along the longitudinal axis of the chamber.

In one embodiment, the chamber has a rectangular, a square, an ovoidal, or a circular cross section over at least a portion of its length, notably over the whole of its length.

In one embodiment, the length of the chamber along the longitudinal axis is greater than 1 cm.

In one embodiment, each of the first or second transfer devices comprises at least one reflector located opposite said at least one acoustic wave generator along the longitudinal axis.

In one embodiment, the reflector is a layer made from a metal, preferably titanium or stainless steel.

In one embodiment, the reflector is a layer of free air, or a foam-like material such as for example cork.

In one embodiment, the reflector is a layer of free air at the outside of the chamber of the transfer device.

In one embodiment, there are multiple reflections of the acoustic waves going back and forth between the first and second walls of the chamber due to a difference in impedance between the reflector, on the one hand, and the fluid and material of the walls, on the other hand.

In one embodiment, the acoustic reflection coefficient of the reflector is ranging from 0.5 to 1, preferably from 0.75 to 1, more preferably from 0.9 to 1. According to one embodiment, the second wall (i.e. the reflector layer) is made from a material exhibiting an acoustic reflection coefficient ranging from 0.5 to 1, preferably from 0.75 to 1, more preferably from 0.9 to 1.

In one embodiment, the reflector comprises a material having an acoustic impedance distinct from the acoustic impedance of the fluid.

In one embodiment, the reflector comprises a material having an acoustic impedance inferior to the acoustic impedance of the fluid.

In one embodiment, the reflector comprises a material having an acoustic impedance superior to the acoustic impedance of the fluid.

In one embodiment, the first and/or second walls of the chamber, preferably both, comprise a material having an acoustic impedance similar to the fluid.

In one embodiment, the second wall, facing the first wall coupled with an acoustic wave generator, comprises a material having an acoustic impedance at least ten times greater than that of the fluid. Using materials having a high acoustic impedance in the walls of the chamber is advantageous as it improves the acoustic focusing of particles by promoting the formation of a prominent pressure extremum.

In one embodiment, the first and/or second walls of the chamber, preferably both, comprise a material selected from the group of: mineral glass, organic glass, quartz, thermoplastic material such as for example PMMA or polycarbonate, metal, or a mixture thereof.

In one embodiment, the first and/or second walls of the chamber may be in the form of plates, portions of cylinders or spheres.

In one embodiment, the first and/or second walls of the chamber are opaque, i.e. the first and/or second walls of the chamber are not optically transparent, i.e. they are not transparent to wavelengths between 200 nm and 50 μm.

In one embodiment, the first and/or second walls of the chamber are optically transparent, i.e. they are transparent to wavelengths between 200 nm and 50 μm. This embodiment is particularly advantageous if it is desirable to acquire images of particles, such as cells, present within the chamber.

In one embodiment, the first transfer device and/or the second transfer device comprise a single inlet in fluid communication with the chamber.

In one embodiment, the first transfer device and/or the second transfer device comprise a plurality of acoustic wave generators arranged along the length of the chamber. Said acoustic wave generators are located on the same side of the chamber. Alternatively, said acoustic wave generators are located opposite each other.

The use of a plurality of acoustic wave generators is advantageous when the fluid flows at high velocity or when layers of large particles are to be generated. In the first case, the flight time under the generators decreases as the fluid velocity increases. This may require a greater number of transducers to be used in order to achieve focusing. In the second case, in the absence of flow for example, it is possible to use a plurality of acoustic wave generators to form layers of large particles.

When a plurality of acoustic wave generators is used, at least one of them may generate an acoustic wave along the width of the chamber.

In one embodiment, the acoustic wave generator is a piezoelectric transducer, a wide-band acoustic wave generator, or an electromagnetic vibrator.

In one embodiment, the acoustic wave generator is external to the chamber.

In one embodiment, the first transfer device and/or the second transfer device further comprise a transmitter layer coupled to the acoustic wave generator.

In one embodiment, the acoustic wave generator is coupled with the first wall of the chamber.

In one embodiment, for example the acoustic wave generator is coupled with the first wall of the chamber by a dry acoustic coupling. In said embodiment, the first wall is the transmitter and the second wall is the reflector layer.

According to one embodiment, the at least one acoustic wave generator is coupled to the first wall (i.e. the transmitter layer) with a coupling layer.

According to one embodiment, said coupling layer is made from thermoplastic elastomers, thermoplastic polyurethanes or silicone.

According to one embodiment, said coupling layer is made of oil or a mixture comprising oil.

According to one embodiment, the acoustic conductance coefficient of the first wall (i.e. the transmitter layer) is ranging from 0.5 to 1, preferably from 0.75 to 1, more preferably from 0.9 to 1. According to one embodiment, the first wall (i.e. the transmitter layer) is made from a material exhibiting an acoustic conductance coefficient ranging from 0.5 to 1, preferably from 0.75 to 1, more preferably from 0.9 to 1.

In one embodiment, the acoustic wave generator is integrated within the first wall of the chamber such as for example by bonding or any other means known in the art.

In one embodiment, the acoustic wave generator may, for example, be fixed to the first wall of the chamber. This fixing may be carried out by any way known to persons skilled in the art, notably by gluing.

In one embodiment, the reflector may, for example, be fixed to the second wall of the chamber. This fixing may be carried out by any way known to persons skilled in the art, notably by gluing.

In one embodiment, the reflector may, for example, be temporarily placed on the second wall of the chamber.

In one embodiment, the acoustic wave generator may be supplied with a sinusoidal voltage. In a variant, the acoustic wave generator may be supplied with a triangular or square-wave voltage.

In one embodiment, the acoustic wave generator may be operated by digital or analog control.

In one embodiment, a layer of acoustic matching material may be present between the acoustic wave generator and the first wall of the chamber. The acoustic matching may be provided by using any material known to persons skilled in the art as suitable for this purpose.

In one embodiment, the acoustic wave generator generates volumetric acoustic waves, surface acoustic waves, standing surface acoustic waves, multi-dimensional acoustic waves or standing acoustic waves.

In one embodiment, the acoustic wave generator generates an acoustic force field over the thickness, not over the width of the chamber. This embodiment is particularly advantageous as it allows the formation of a layer of particles.

In one embodiment, the acoustic wave generator generates an acoustic force field over the thickness and over the width of the chamber. This embodiment is particularly advantageous as it may be possible to move a group of particles depending of their sizes in any area of the chamber, and thus to sort and fractionate a particle suspension such as a biological fluid.

In one embodiment, the acoustic waves have an incident angle to the longitudinal axis of the chamber ranging from 85° to 95°, e.g. from 89° to 91°.

In one embodiment, the acoustic waves have an incident angle to the longitudinal axis of the chamber of substantially 90°.

In one embodiment, the acoustic waves have a wavelength $\lambda$ ranging from 5 µm to 2 cm.

In one embodiment, the acoustic wave generator operates at a frequency f which can be different from a resonance frequency $f_0$ of the chamber along the second transverse axis.

The expression "$f_0$ being a resonance frequency of the chamber along the second transverse axis" signifies that $f_0$ is such that the thickness $\underline{e}$ of the chamber, measured at a given position along the longitudinal axis of the chamber, is determined by $$e = \frac{n\lambda}{2},$$

where n is an integer and $$\lambda = \frac{c_f}{f_0}$$

where $c_f$ denotes the speed of sound in the fluid present within the chamber, at the temperature of the fluid, for example 20° C. In other words, the frequency $f_0$ is equal to the theoretical frequency which, at a given position along the longitudinal axis of the chamber, meets the condition of resonance of the acoustic wave in the chamber and gives rise to the formation of a standing wave along its second transverse axis, in other words along its thickness.

In one embodiment, the acoustic wave generator operates at a frequency equal to or less than 100 MHz, and notably in the range from 0.05 to 100 MHz. This embodiment is particularly advantageous as it allows handling living cells without damaging them.

In one embodiment, the acoustic wave generator preferably operates at a frequency f which is different from $f_0$ and is in the range from $0.75f_0$ to $1.25f_0$.

In one embodiment, at least one layer of particles, for example cells, is formed by acoustic focusing.

In one embodiment, at least one extremum of acoustic pressure is formed within the fluid by the generated acoustic waves.

The layer of particles is preferably focused at an extremum of acoustic pressure (acoustic node or antinode) formed within the fluid by the generated acoustic waves. For example, a plurality of layers of distinct particles is formed, each of these layers being present at a distinct acoustic pressure extremum.

In this embodiment, a layer of cells may be formed in the chamber at an extremum of acoustic pressure, allowing the enrichment of the fluid in the first container with said cells.

The layer of particles that is formed may have a shape which is elongated along the longitudinal axis of the chamber, and may be, for example, oval or rectangular in shape when viewed in a direction perpendicular to the focusing plane. In a variant, the layer of particles that is formed may have a circular or square shape when viewed in a direction perpendicular to its focusing plane.

In one embodiment, the fluidic connection between the different parts of the system comprise any means known by one skilled in the art, such as flexible manifolds or tubes and clamps or valves. Their representations in the drawings are not representative of their dimensions and positions.

In one embodiment, the system of the invention further comprises a third container and a third transfer device.

In one embodiment, the system of the invention comprises a plurality of containers and a plurality of transfer devices. In this embodiment, each container may be connected to one transfer device, i.e. the number of containers is equal to the number of transfer devices, or each container may be connected to more than one transfer device, typically two transfer devices. This embodiment is particularly advantageous as it allows the separation of more than one group of particles in a fluid.

In one embodiment, the system of the invention may further comprise several devices designed to allow measurements through non-invasive means comprising but not limited to acoustical, optical or electromagnetic means.

The present invention also relates to a method for changing a concentration of at least one given group of particles comprised in a fluid, by means of a system comprising:

a first container and a second container;
a first transfer device and a second transfer device each comprising:
  a chamber configured to be associated with at least one acoustic wave generator for generating acoustic waves within the chamber;
  an inlet and at least two outlets comprising a first outlet for fluid enriched with said given group of particles and a second outlet for fluid depleted of said given group of particles;
the method comprising preliminary steps of:
  (a) introducing a volume of fluid in the first container and a volume of fluid in the second container;
  (b) applying an acoustic field by generating acoustic waves inside the chamber of each of the first and second transfer devices;
followed by steps of:
  (c) simultaneously transferring fluid contained in the first container into the chamber of the first transfer device, and transferring fluid contained in the second container into the chamber of the second transfer device;
  (d) simultaneously transferring fluid enriched with said given group of particles, collected from the first outlet of the first and second transfer devices, into the first container, and transferring fluid depleted of said given group of particles, collected from the second outlet of the first and second transfer devices, into the second container;
  wherein the respective volumes of fluid in the first and second containers are kept constant during steps (c) and (d).
In one embodiment, the method comprises steps of:
(a') providing a system of the invention as described above;
(a) introducing a volume of fluid in the first container and a volume of fluid in the second container;
(b) applying an acoustic field by generating acoustic waves inside the chamber of each of the first and second transfer devices;
followed by steps of:
(c) simultaneously transferring fluid contained in the first container into the chamber of the first transfer device, and transferring fluid contained in the second container into the chamber of the second transfer device;
(d) simultaneously transferring fluid enriched with said given group of particles, collected from the first outlet of the first and second transfer devices, into the first container, and transferring fluid depleted of said given group of particles, collected from the second outlet of the first and second transfer devices, into the second container;
wherein the respective volumes of fluid in the first and second containers are kept constant during steps (c) and (d).

The method of the invention is a simple and fast method for separating at least one given group of particles in a fluid.

The method of the invention also enables filterless filtration to be carried out by selective acoustic focusing of the handled particles.

In one embodiment, the method is implemented by the system of the invention as described above.

In one embodiment, the system of the invention is associated with at least one acoustic wave generator for generating acoustic waves within the chamber of each transfer device.

In one embodiment, step (c) and step (d) are simultaneous.

In one embodiment, the fluid is circulated continuously from one of the first and second containers, through one of the first and second transfer devices, and to one of the first and second containers.

In one embodiment, the method of the invention comprises the measurement of the volume of fluid in the first container and/or the second container, and/or the weight of the first container and/or the second container, and/or the fluid flow rate in the first container and/or the second container.

In one embodiment, flow control means are provided for applying a controlled flow, notably from the outlets of the containers to the inlets of the transfer devices and from the outlets of the transfer devices to the inlets of the containers.

According to one embodiment, said flow control means comprise a control unit, measurement means and flowing means.

According to one embodiment, the control unit is configured to keep the volume of fluid in each of the first and second containers constant by regulating the flow rate of the fluid circulating in the system as a function of measurements representative of the volume of fluid in the first container and/or the second container. In this embodiment, the flow of the fluid in the system is preferably controlled at all times.

In one embodiment, the measurement means are configured to measure the volume of fluid in the first container and/or the second container, and/or the weight of the first container and/or the second container, and/or the fluid flow rate in the first container and/or the second container. For example, measurement means can be weighing scales, flowmeters or any other means for measuring a weight, a volume, a flow, or any other value representative of a volume known in the art.

In one embodiment, the measurements representative of the volume of fluid in the first container and/or the second container are measurements of the volume of fluid in the first container and/or the second container, and/or measurements of the weight of the first container and/or the second container, and/or measurements of the fluid flow rate in the first container and/or the second container.

In one embodiment, the first container and/or the second container are weighed in real time to ensure that their weights stay constant and the flow rates are electronically regulated.

In one embodiment, the flowing means are configured to regulate flow rates at the inlets of the first and second containers and the first and second transfer devices. In this embodiment, said flowing means work in cooperation with the measurement means to ensure that the volume of fluid in each of the first and second container is constant. Typically, the flow rate imposed by the flowing means is controlled by the measurement means that measure the volume or weights of the containers.

In one embodiment, the flowing means are located at the outlets of the first and second containers and the first and second transfer devices.

In one embodiment, the flowing means comprise a pump, such as for example a peristaltic pump, gear pump, centrifugal pump, diaphragm pump, rotary vane pump, piston pumps, pressure pumps, gravitational forces, and their derivatives. In one embodiment, the flowing means comprise valves. In this embodiment, said flowing means regulate the flow rates at the inlets of the first and second containers and of the chamber to prevent a complete emptying of the first and/or second containers.

In one embodiment, the fluid flow rate at the inlet of each of the first and second transfer devices is between 0.1 mL/min and 50 mL/min.

In one embodiment, the fluid flow rate at the inlet of each of the first and second containers is between 0.1 mL/min and 50 mL/min.

In one embodiment, the method comprises the regulation of the respective flow rates at the inlets of the first and second containers and the first and second transfer devices as a function of measurements representative of the volume of fluid in the first container and/or the second container.

In one embodiment, the steps (c) and (d) are repeated until the concentration of the given group of particles in the fluid reaches a predefined level in the second container. In this embodiment, the fluid comprised in the containers repeatedly circulates in the transfer devices until a predefined level of the given group of particles concentration is reached in the second container, i.e. to enrich the fluid in the first container with at least one group of particles and simultaneously deplete the fluid in the second container with said group of particles. In this embodiment, the method is a closed-loop method, or a continuous loop method.

In one embodiment, said predefined level is equal or lower than the initial level.

In one embodiment, the steps (c) and (d) are repeated until the concentration of the given group of particles in the fluid is inferior or equal to a negligible level in the second container.

In one embodiment, said negligible level is inferior or equal to a required purity level. In the case of blood plasma, EU requirements are $50 \times 10^9$ platelets per liter, $6 \times 10^9$ red blood cells per liter and $0.1 \times 10^9$ white blood cells per liter.

In one embodiment, the method further comprises a step of fluid sampling from a subject.

In one embodiment, the fluid can be sampled from a subject for example by blood sampling, blood donation, urine sampling, stool sampling, organ donation, lombar puncture, cord blood donation, bone marrow harvest, milking, milk donation, seashell mixing, biopsy or any procedure known in the art.

In one embodiment, the fluid can be sampled from the environment for example by water sampling, mud sampling or any procedure known in the art.

In one embodiment, a fluid enriched with blood cells is collected in the first container and plasma depleted of blood cells is collected in the second container.

In one embodiment, a fluid enriched with platelets is collected in the first container and plasma is collected in the second container.

In one embodiment, a fluid enriched with blood cells is collected in the first container and blood depleted of blood cells is collected in the second container.

In one embodiment, a fluid enriched with platelets is collected in the first container and a fluid depleted of platelets and comprising red blood cells and white blood cells is collected in the second container.

In one embodiment, a fluid enriched in Langerhans islets is collected in the first container and a fluid depleted of Langerhans islets is collected in the second container.

In one embodiment, a fluid enriched in stem cells is collected in the first container and a fluid depleted of stem cells is collected in the second container.

In one embodiment, a fluid enriched in megakaryocytes is collected in the first container and a fluid depleted of megakaryocytes is collected in the second container.

In one embodiment, a fluid enriched in liposomes is collected in the second container and a fluid depleted of liposomes is collected in the first container.

In one embodiment, a fluid enriched in microorganisms is collected in the first container and a fluid depleted of microorganisms is collected in the second container.

In one embodiment, a fluid enriched in circulating cells is collected in the first container and a fluid depleted of circulating cells is collected in the second container.

In one embodiment, a fluid enriched in parasites is collected in the first container and a fluid depleted of parasites is collected in the second container.

In one embodiment, a fluid enriched in milk fat is collected in the second container and a fluid depleted of milk fat is collected in the first container.

In one embodiment, a fluid enriched in particles is collected in the first container and a fluid depleted of particles is collected in the second container.

In one embodiment, a fluid enriched in microbubbles is collected in the second container and a fluid depleted of microbubbles is collected in the first container.

In one embodiment, the method further comprises a final step of returning or re-administrating fluid enriched with at least one given group of particles to a subject. In one embodiment, the method further comprises a step of re-administration of the fluid enriched with at least one given group of particles to a subject who provided the initial sample of fluid.

In one embodiment, the method of the invention may enable at least one layer of particles, such as cells, to be formed by acoustic focusing. In particular, the method of the invention may comprise a step in which at least two chemical species, or two types of cells, present in the layer formed by acoustic focusing are made to react.

In one embodiment, the method of the invention may further comprise several steps between steps (c) and (d) to allow measurements through noninvasive means comprising but not limited to acoustical, optical or electromagnetic means and thus control the acoustic generator and/or the flowing means allowing a perfect control of the final products in the first and second container.

The present invention also relates to a use of the system of the invention or the method of the invention.

In one embodiment, the system of the invention or the method of the invention is used for fluid enrichment, or fluid fractionation.

In one embodiment, the system of the invention or the method of the invention is used for particle manipulation such as for example cell manipulation, particle separation such as for example cell separation, particle washing such as for example cell washing, particle counting such as for example cell counting, particle sorting such as for example cell sorting, particle concentration, particle elimination, particle isolation. Said particles may be cells, microorganisms, organelles, bacteria, viruses, parasites, sand, sediment, plankton, algae, cell clusters, tissue, proteins, microbubbles, fat, pollen, spores, metal particles, parasite eggs or a mixture thereof.

In one embodiment, the system of the invention or the method of the invention is used for cell therapy, such as for example cell washing and cell sorting.

In one embodiment, the system of the invention or the method of the invention is used for flow cytometry.

In one embodiment, the system of the invention or the method of the invention is used in methods of sorting species; methods of diagnosis or analysis; methods of purification, enrichment or depletion of species; methods of synthesis of species; methods of modification of physical or chemical characteristics of species; methods of medicinal product research; or methods of mixing or methods of measuring diffusion coefficients.

In one embodiment, the system of the invention or the method of the invention is used for regenerative medicine. In this embodiment, the enriched fluid can be administrated to a subject to ensure regeneration of tissue or fluid.

In one embodiment, the system of the invention or the method of the invention is used for depolluting water, oil or petroleum, for example in a mining or drilling facility.

In the present invention, the following terms have the following meanings:

"Blood" refers to the combination of blood cells suspended in plasma and/or additive solutions.

"Blood cells" refers to red blood cells, white blood cells and platelets.

"Buffy coat" refers to the suspension containing most of the white blood cells and platelets obtained after centrifugation of whole blood (thin layer between the layer of plasma and the layer of red cells).

"Cell cluster" refers to an agglomerate or a group of cells.

"Cell processing" refers to any process applied to cell suspensions with diagnosis or production purposes "Cell suspension" refers to a mixture of cells or a single type of cells suspended in a medium, preferably a liquid medium.

"Constant volume" refers to a volume having a deviation of less than 10%, preferably less than 1%.

"Depleted fluid" or impoverished fluid refers to a fluid that has lost at least 50% of a given group of particles compared to its initial concentration.

"Enriched fluid" refers to a fluid that has gained at least 50% of a given group of particles compared to its initial concentration.

"Fluidly connected" refers to several parts of a device connected using tubing in such a way that fluid can be safely transferred from one to another.

"Longitudinal axis of the chamber" refers to the line joining the set of centers of the cross sections of the chamber. The longitudinal axis of the chamber may be straight or curved and may be contained in a plane which may be a plane of symmetry for some or all of the cross sections of the chamber.

"Particle" refers to any objects, components or cells comprised in a fluid.

"Plasma" refers to the liquid component of blood wherein red blood cells, white blood cells and platelets have been removed.

"Platelets" refers to anucleate cells involved in the cellular mechanisms of primary hemostasis leading to the formation of blood clots. The terms platelets or thrombocytes can be used interchangeably.

BRIEF DESCRIPTION OF THE DRAWINGS

The following detailed description will be better understood when read in conjunction with the drawings. For the purpose of illustrating, the system is shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

Features and advantages of the invention will become apparent from the following description of embodiments of a system, this description being given merely by way of example and with reference to the appended drawings in which.

While various embodiments have been described and illustrated, the detailed description is not to be construed as being limited hereto. Various modifications can be made to the embodiments by those skilled in the art without departing from the true spirit and scope of the disclosure as defined by the claims.

DETAILED DESCRIPTION

Figure 1:
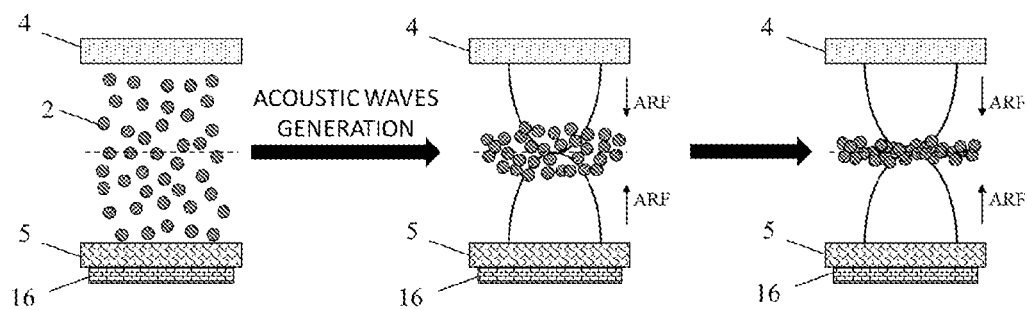
FIG. 1 is a schematic representation of the application of an acoustic field on particles within a chamber.

As shown in FIG. 1, the application of an acoustic field on particles 2 within a chamber between an acoustic wave generator 16 and a reflector 4 induces a movement of said particles 2, allowing to gather said particles 2 at a node of said acoustic field.

In this example, ultrasonic waves are generated in a chamber between a reflector 4 and a wall 5 associated with an acoustic wave generator 16 coupled with a transmitter layer. This enables the creation of an acoustic pressure node in the center of the chamber (depending on the chosen frequency at which the acoustic wave generator 16 operates) and therefore of acoustic radiation forces (ARF). The ARF push the particles 2 towards the pressure node with a force of up to a hundred times gravity equivalent. The particles 2 suspended in the fluid will then migrate to the sound pressure node and can then remain trapped in this position.

A plurality of acoustic nodes can be created in the chamber, said acoustic nodes can be located at the center of the chamber, or off the center of the chamber.

This is particularly advantageous as it allows the isolation of particles 2 within a fluid without any mechanical force, filtration, or centrifugation steps that could damage said particles 2, especially if said particles 2 are fragile like cells.

Figure 2:
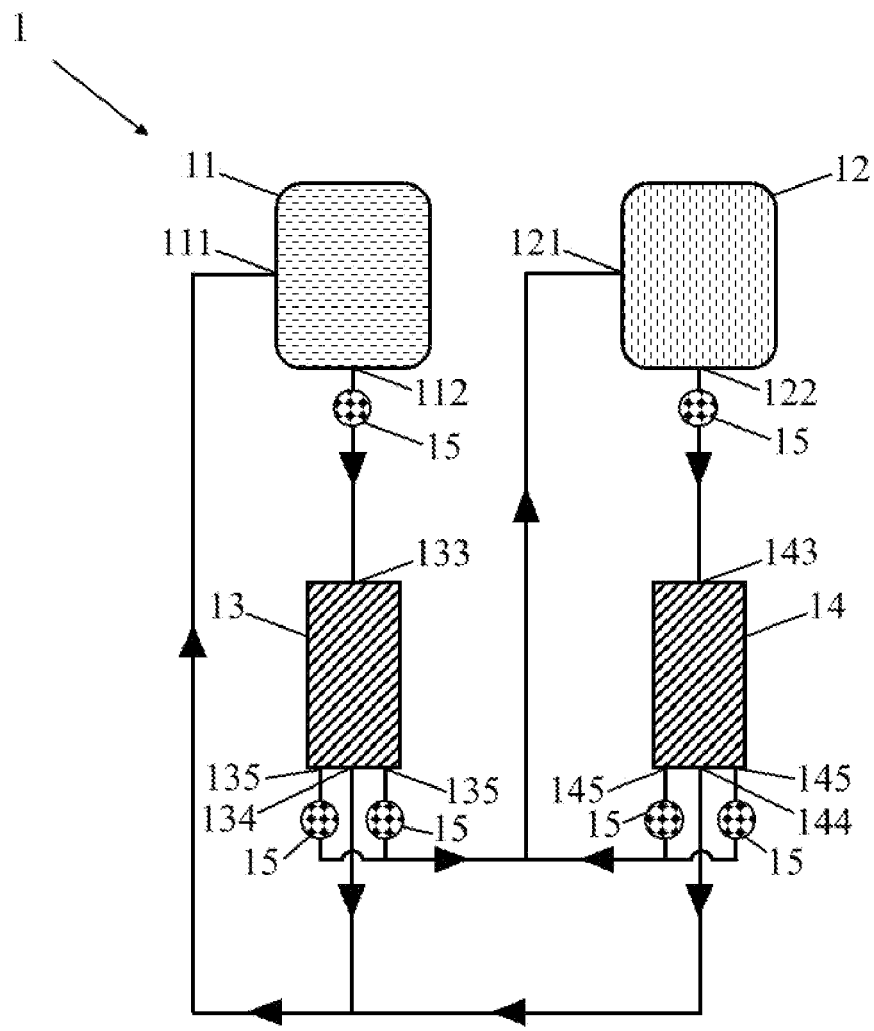
FIG. 2 is a schematic representation of a system according to a first embodiment of the invention.
Figure 3:
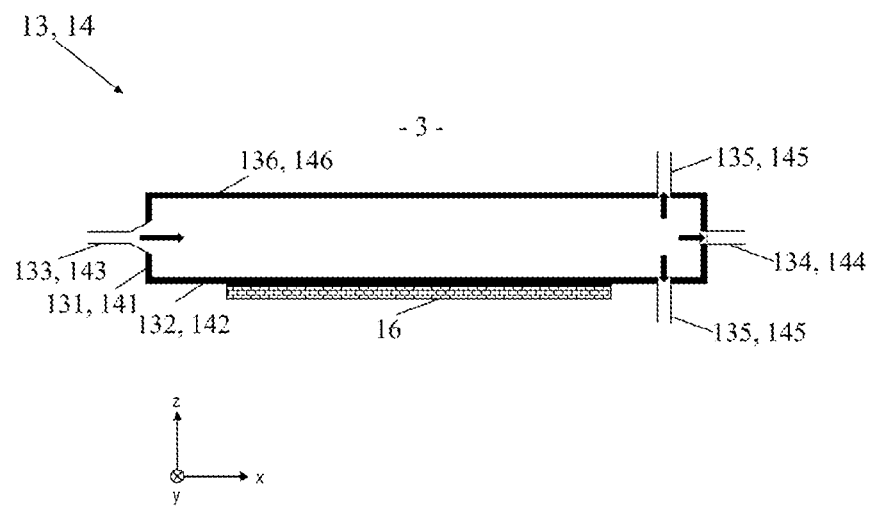
FIG. 3 is a schematic representation of a transfer device of the system of FIG. 2.

In the first embodiment shown in FIG. 2 and FIG. 3, the system 1 according to the invention comprises:

a first container 11 comprising an inlet 111 and an outlet 112;

a second container 12 comprising an inlet 121 and an outlet 122;

a first transfer device 13 and a second transfer device 14, wherein the first container 11 is fluidly connected to an inlet 133 of the first transfer device 13 and the second container 12 is fluidly connected to an inlet 143 of the second transfer device 14, each of the first and second transfer devices 13, 14 comprising:

a chamber 131, 141;

three outlets 134, 135, 144, 145 comprising a first central outlet 134, 144 for fluid enriched with said given group of particles and two second peripheral outlets 135, 145 for fluid depleted of said given group of particles;

pumps 15 configured to regulate flow rates at the inlets 111, 121, 133, 143.

FIG. 3 shows a schematic larger-scale view of the chamber 131 or 141 of the transfer devices 13, 14 comprised in the system represented in FIG. 2.

In this embodiment, the first and second containers 11, 12 are each configured to comprise a fluid, the fluid comprised in the first container 11 being enriched with at least one group of particles and the fluid comprised in the second container 12 being depleted of said group of particles.

In this embodiment, operating the system 1 comprises the following: a volume of fluid is introduced in the first container 11 and a volume of fluid is introduced in the second container 12; an acoustic field is applied to said fluid by generating acoustic waves inside the chamber 131, 141 of each of the first and second transfer devices 13, 14; then the fluid contained in the first container 11 is transferred into the chamber 131 of the first transfer device 141, and the fluid contained in the second container 12 is simultaneously transferred into the chamber 141 of the second transfer device 14, whereby a given group of particles migrates to a sound pressure node in the chamber 13, 14 created by the generation of an acoustic field in said chamber 131, 141 and are delivered at the central outlet 134, 144 whereas other components of the fluid are delivered on the sides of the chamber 131, 141 at the peripheral outlets 135, 145; the fluid enriched with said given group of particles, collected from the central outlet 134, 144 of the first and second transfer devices 13, 14, is transferred into the first container 11, and the fluid depleted of said given group of particles, collected from the peripheral outlets 135, 145 of the first and second transfer devices 13, 14, is simultaneously transferred into the second container. The respective volumes of fluid in the first and second containers are kept constant during operating through the regulation of the flow rate of the fluid circulating in the system 1, obtained by means of the pumps 15, as a function of measurements representative of the volume of fluid in the first container 11 and/or the second container 12.

This embodiment is particularly advantageous as the given group of particles is separated from other components of the fluid without using any mechanical force, thus preventing any damage to said given group of particles.

This embodiment is particularly advantageous as the flow rates at the inlets 111, 121, 133, 143 of the containers and chambers are regulated to ensure that the volume of fluid in each of said containers 11, 12 stays constant at all times, preventing an inopportune emptying of one of said containers 11, 12. By keeping these volumes constant, the volumes and particle concentrations of the final products are perfectly controlled.

As shown in FIG. 3, in this embodiment, each transfer device 13, 14 comprises:
- a chamber 131, 141 configured to be associated with an acoustic wave generator 16 for generating acoustic waves;
- a reflector located opposite said at least one acoustic wave generator 16, the reflector being the air 3 surrounding the chamber 131, 141 in this example; and
- three outlets 134, 135, 144, 145 comprising a first central outlet 134, 144 for fluid enriched with said given group of particles and two second peripheral outlets 135, 145 for fluid depleted of said given group of particles.

In this embodiment, the chamber 131, 141 of each transfer device 13, 14 extends along a longitudinal axis (x), has a cross section with a width measured along a first transverse axis (y) and a thickness measured along a second transverse axis (z) perpendicular to the first transverse axis, the width being greater than or equal to the thickness, the chamber 131, 141 having first and second walls 132, 136, 142, 146 along the second transverse axis (z). The chamber 131, 141 has a thickness between 350 and 450 µm, a width between 0.7 and 2.1 cm and a length between 1 and 6 cm and the walls 132, 136, 142, 146 are made of PMMA.

In this embodiment, the fluid is introduced at the inlet 133, 143 of the chamber 131, 141. The flow rate at the inlet 133, 143 of the chamber 131, 141 ranges between 0.4 and 0.6 mL/min. The acoustic generator 16 associated with said chamber 131, 141 generates acoustic waves having a frequency ranging between 1.8 and 2 MHz in the chamber 131, 141 that are reflected by the reflector being the air 3 located at the outside of the chamber 131, 141. This creates at least one pressure node in the chamber 131, 141 allowing a selective migration of a given group of particles towards the central outlet 134, 144 while the other components of the fluid are evacuated at the peripheral outlets 135, 145. The acoustic wave generator 16 can be coupled with a transmitter layer (not represented in FIG. 3).

This embodiment is particularly advantageous as an acoustic field is generated within the chamber 131 by the acoustic wave generator 16. As explained in FIG. 1, this simple arrangement allows the isolation of particles within a fluid without any mechanical force, filtration, or centrifugation steps that could damage said particles, especially if said particles are fragile like cells.

Figure 4:
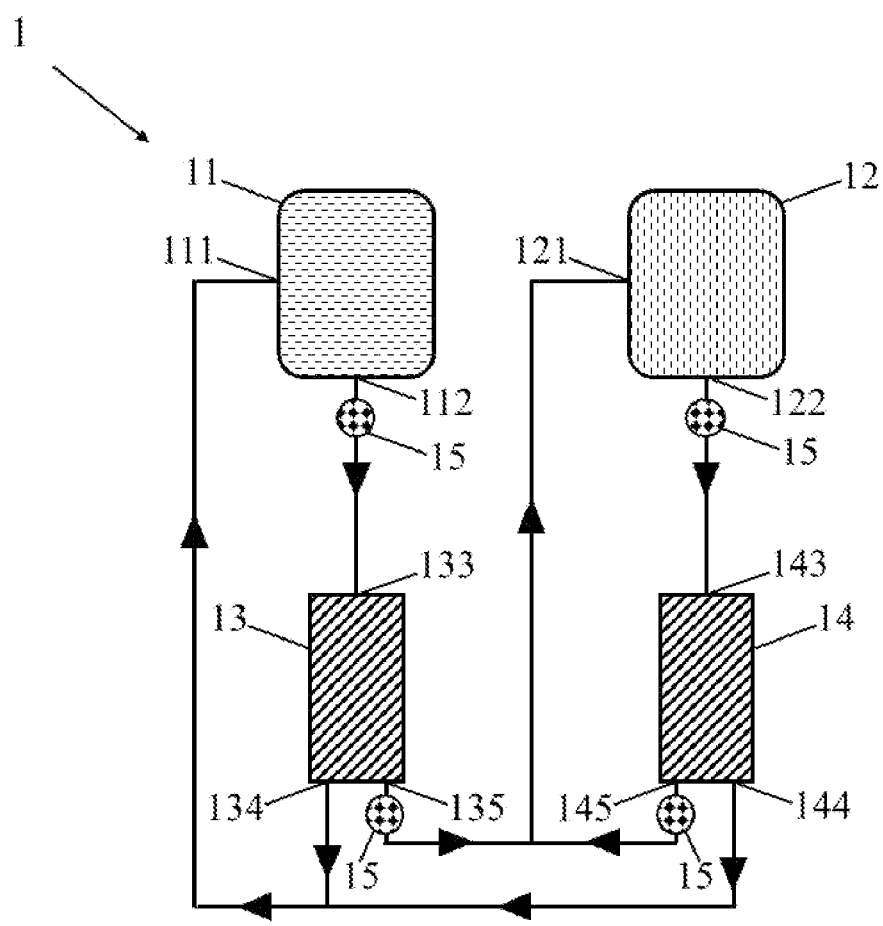
FIG. 4 is a schematic representation of a system according to a second embodiment of the invention.

In the second embodiment shown in FIG. 4, the elements similar to those of the first embodiment bear identical references. The system 1 of the second embodiment differs from the first embodiment in that each transfer device 13, 14 comprises only two outlets. More precisely, the system 1 according to the second embodiment of the invention comprises:
- a first container 11 comprising an inlet 111 and an outlet 112;
- a second container 12 comprising an inlet 121 and an outlet 122;
- a first transfer device 13 and second transfer device 14, wherein the first container 11 is fluidly connected to an inlet 133 of the first transfer device 13 and the second container 12 is fluidly connected to an inlet 143 of the second transfer device 14, each of the first and second transfer devices 13, 14 comprising:
  - a chamber 131, 141;
  - two outlets 134, 135, 144, 145 comprising a first outlet 134, 144 for fluid enriched with said given group of particles and a second outlet 135, 145 for fluid depleted of said given group of particles;
- pumps 15 configured to regulate flow rates at the inlets of the first and second containers and the chambers 111, 121, 133, 143.

In this embodiment, the first and second containers 11, 12 are each configured to comprise a fluid, the fluid comprised in the first container 11 being enriched with at least one group of particles and the fluid comprised in the second container 12 being depleted of said group of particles.

In this embodiment, the respective volumes of fluid in the first and second containers 11, 12 are kept constant at all times.

This embodiment is particularly advantageous as the flow rates at the inlets of the containers and chambers 111, 121, 133, 143 are regulated to ensure that the volume of fluid in each of said containers 11, 12 stays constant at all times, preventing an inopportune emptying of one of said containers 11, 12.

Figure 5:
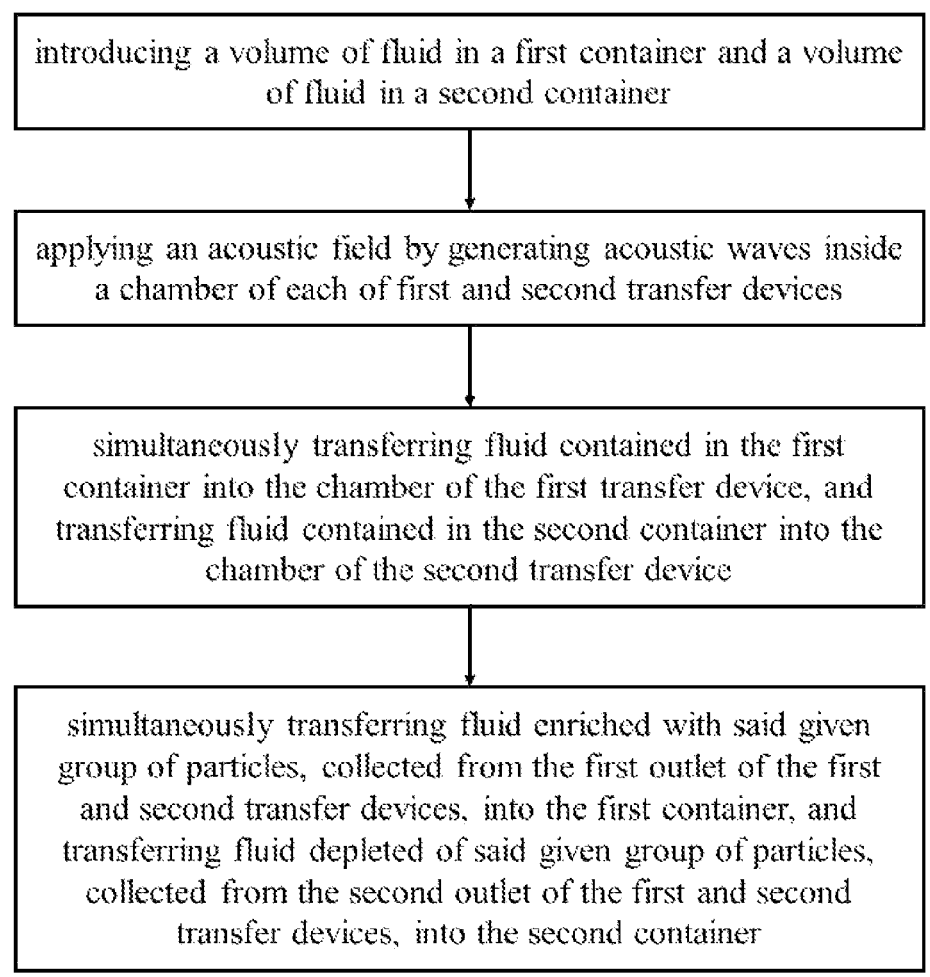
FIG. 5 is a flow chart showing steps of a method according to one embodiment of the invention.

As shown in FIG. 5, the method of the invention comprises the following steps:
providing a system 1 of the invention;
applying an acoustic field by generating acoustic waves inside each chamber 131, 141 of the first and second transfer devices 13, 14, by means of each acoustic wave generator 16;
simultaneously transferring the fluid contained in the first container 11 to the first transfer device 13, and transferring the fluid contained in the second container 12 to the second transfer device 14;
simultaneously transferring the fluid enriched with at least one group of particles, collected from the first outlet(s), to the first container 11 and the fluid depleted of said group of particles, collected from the second outlet(s), to the second container 12.

In addition, the flow rates at the inlets 111, 121, 133, 143 of the first and second containers 11, 12 and the chambers 131, 141 are regulated so that the respective volumes of fluid in the first and second containers 11, 12 are kept constant during the steps of the method.

As illustrated above, the method of the invention is a simple and fast method for separating at least one group of particles from a fluid without any dilution required. Furthermore, no steps of filtration, centrifugation or any steps requiring mechanical forces are needed during said method. This prevents damage to the group of particles to be separated.

EXAMPLES

The present invention is further illustrated by the following examples. The following examples are implemented, in particular, using the system of FIGS. 2 and 3.

Example 1

Platelet Enrichment

Materials and Methods

Platelet rich plasma is injected in equal amount in the first and second container of the present invention, hence each of them holds 50% of the total amount of platelets in the system. The platelet concentration may vary from high concentration to diluted samples. The platelets have an average diameter of 2 µm.

A flow is induced through the transfer devices by the flowing means. The flow control means are activated so each container holds a constant volume of fluid through the process with the flow rate controlled accordingly. The flow in the transfer devices inlets is kept within 0.4 to 0.6 mL/min. The transfer devices chambers have a thickness between 350 and 450 µm, a width between 0.7 and 2.1 cm and a length between 1 and 6 cm.

An acoustic force field is induced in the transfer device by means of the acoustic wave generator. The frequency of the acoustic wave is set between 1.8 and 2 MHz with a sinusoidal waveform.

Results

The first container is enriched with platelets while the second container is depleted of platelets until a predefined platelet level is reached in the second container. After 2.5 hours of processing, the first container holds between 60 and 80% of the platelets while the second container holds between 20 and 40% of the platelets.

Example 2

Blood Fractionation

Materials and Methods

Diluted whole blood is injected in equal amount in the first and second container of the present invention, hence each of them holds 50% of the total amount of blood cells in the system. The concentration of blood cell may vary from high concentration to diluted samples. Red blood cells have an average diameter of 6 µm while the platelets have an average diameter of 2 µm.

A flow is induced through the transfer devices by the flowing means. The flow control means are activated so that each container holds a constant volume of fluid through the process with the flow rate controlled accordingly. The flow in the transfer devices inlets is kept within 0.6 to 1 mL/min. The transfer devices chambers have a thickness between 350 and 450 µm, a width between 0.7 and 2.1 cm and a length between 1 and 6 cm.

An acoustic force field is induced in the transfer device by means of the acoustic wave generator. The frequency of the acoustic wave is set between 1.8 and 2 MHz with a sinusoidal waveform. This acoustic force field induce the migration of red blood cells toward the central outlet while the platelets tend to stay in the lateral outlets.

Results

The first container is enriched with red blood cells while the second container is depleted of red blood cells until a predefined red blood cell level is reached in the second container. After 2.5 hours of processing, the first container holds between 95 and 99% of the red blood cells while the second container holds between 1 and 5% of the red blood cells.

The invention claimed is:

1. A system for changing a concentration of at least one given group of particles comprised in a fluid, the system comprising: a first container and a second container; a first transfer device and a second transfer device, wherein the first container is fluidly connected to an inlet of the first transfer device and the second container is fluidly connected to an inlet of the second transfer device, each of the first and second transfer devices comprising: a chamber configured to be associated with at least one acoustic wave generator for generating at least one acoustic wave within the chamber; at least two outlets comprising a first outlet for fluid enriched with said given group of particles and a second outlet for fluid depleted of said given group of particles; the first outlet being fluidly connected to the first container and the second outlet being fluidly connected to the second container; and means for keeping the volume of fluid in each of the first and second containers constant.

2. The system according to claim 1, wherein the first and second transfer devices comprise at least three outlets wherein one of the at least three outlets is the first outlet which is a first central outlet for fluid enriched with said given group of particles and wherein the remaining at least two outlets comprise the second outlet and at least a third outlet where the second and at least a third outlet are peripheral outlets for fluid depleted of said given group of particles.

3. The system according to claim 1, comprising a control unit configured to keep the volume of fluid in each of the first and second containers constant by regulating the flow rate of the fluid circulating in the system as a function of measurements representative of the volume of fluid in the first container and/or the second container.

4. The system according to claim 3, wherein the measurements representative of the volume of fluid in the first container and/or the second container are measurements of the volume of fluid in the first container and/or the second container, and/or measurements of the weight of the first container and/or the second container, and/or measurements of the fluid flow rate in the first container and/or the second container.

5. The system according to claim 1, comprising measurement means for measuring the volume of fluid in the first container and/or the second container, and/or the weight of the first container and/or the second container, and/or the fluid flow rate in the first container and/or the second container.

6. The system according to claim 1, wherein the chamber of each transfer device extends along a longitudinal axis, has a cross section with a width measured along a first transverse axis and a thickness measured along a second transverse axis perpendicular to the first transverse axis, the width being greater than or equal to the thickness, the chamber having first and second walls along the second transverse axis.

7. The system according to claim 6, wherein a ratio of the width of the chamber to the thickness of the chamber is greater than 1.

8. The system according to claim 6, wherein the at least one acoustic wave has a wavelength $\lambda$ and the thickness of the chamber is substantially equal to a multiple of $\lambda/4$ and in a range from 10 μm to 1 mm.

9. The system according to claim 1, wherein the flow rate at the inlet of each of the first and second transfer devices is between 0.1 mL/min and 50 mL/min.

10. The system according to claim 1, wherein the fluid is a biological fluid selected from the group consisting of human and/or non-human cell suspension, cell cluster suspension, blood, whole blood, surgical blood, platelet rich plasma, buffy coat, urine, serum, lymph, fluidified feces, adipose tissue, bone marrow, cerebrospinal fluid, sperm, cord blood, milk, saliva, tissue, egg albumen, seashell mix, and a mixture thereof.

11. The system according to claim 1, wherein the particles are selected from the group consisting of biological cells, dispersed cells in a dispersion medium, monodis perse or polydisperse cells, blood cells, platelets, red blood cells, white blood cells, cancer cells, bacteria, proteins, liposomes, organelles, cell clusters, viruses, vesicles, microparticles, nanoparticles, microbubbles, microbeads, microorganisms, parasites, algae, sand, sediment, dust, antibodies, powders, gametes, parasite eggs, plankton, tissue, fat, pollen, spores, metal particles, and a mixture thereof.

12. A method for changing a concentration of at least one given group of particles comprised in a fluid, by means of a system comprising:
  a first container and a second container;
  a first transfer device and a second transfer device each comprising:
    a chamber configured to be associated with at least one acoustic wave generator for generating acoustic waves within the chamber;
    an inlet and at least two outlets comprising a first outlet for fluid enriched with said given group of particles and a second outlet for fluid depleted of said given group of particles;
  the method comprising preliminary steps of:
    (a) introducing a volume of fluid in the first container and a volume of fluid in the second container;
    (b) applying an acoustic field by generating acoustic waves inside the chamber of each of the first and second transfer devices;
  followed by steps of:
    (c) simultaneously transferring fluid contained in the first container into the chamber of the first transfer device, and transferring fluid contained in the second container into the chamber of the second transfer device;
    (d) simultaneously transferring fluid enriched with said given group of particles, collected from the first outlet of the first and second transfer devices, into the first container, and transferring fluid depleted of said given group of particles, collected from the second outlet of the first and second transfer devices, into the second container;
  wherein the respective volumes of fluid in the first and second containers are kept constant during steps (c) and (d).

13. The method according to claim 12, wherein the fluid is circulated continuously from one of the first and second containers, through one of the first and second transfer devices, and to one of the first and second containers.

14. The method according to claim 12, further comprising measuring at least one of:
  the volume of the fluid in the first container and/or the second container, a weight of the first container and/or the second container, or a flow rate of the fluid in the first container and/or the second container.

15. The method according to claim 14, further comprising regulating the flow rate of the fluid at the inlets of the first and second containers and the first and second transfer devices as a function of the volume of the fluid measured in the first container and/or the second container.

16. The method according to claim 12, wherein the steps (c) and (d) are repeated until a group of particles in the fluid contained in the second container reaches a predefined concentration.

* * * * *